(12) United States Patent
Charlton

(10) Patent No.: US 10,132,791 B2
(45) Date of Patent: Nov. 20, 2018

(54) BOTTLED GLUCOSE SENSOR WITH NO HANDLING

(71) Applicant: Ascensia Diabetes Care Holdings AG, Basel (CH)

(72) Inventor: Steven C. Charlton, Osceola, IN (US)

(73) Assignee: Ascensia Diagnostics Care Holdings AG, Basel (CH)

( * ) Notice: Subject to any disclaimer, the term of this patent is extended or adjusted under 35 U.S.C. 154(b) by 229 days.

(21) Appl. No.: 15/184,391

(22) Filed: Jun. 16, 2016

(65) Prior Publication Data

US 2016/0299123 A1  Oct. 13, 2016

Related U.S. Application Data

(62) Division of application No. 13/800,799, filed on Mar. 13, 2013, now Pat. No. 9,376,708.

(51) Int. Cl.
| | |
|---|---|
| *G01N 33/00* | (2006.01) |
| *G01N 33/487* | (2006.01) |
| *C12Q 1/54* | (2006.01) |
| *C12Q 1/00* | (2006.01) |
| *G01N 33/52* | (2006.01) |
| *G01N 33/543* | (2006.01) |
| *G01N 21/84* | (2006.01) |

(52) U.S. Cl.
CPC ....... *G01N 33/48757* (2013.01); *C12Q 1/005* (2013.01); *C12Q 1/54* (2013.01); *G01N 21/8483* (2013.01); *G01N 33/52* (2013.01); *G01N 33/5438* (2013.01)

(58) Field of Classification Search
CPC ................................. G01N 33/48757
USPC .......................................................... 422/50
See application file for complete search history.

(56) References Cited

U.S. PATENT DOCUMENTS

| | | | |
|---|---|---|---|
| 2,944,661 | A | 7/1960 | Goldstein |
| 3,194,426 | A | 7/1965 | Brown |
| 3,592,356 | A | 7/1971 | Rovin |
| 3,651,585 | A | 3/1972 | Perrella et al. |
| 3,717,282 | A | 2/1973 | Nordskog |
| 4,218,421 | A | 8/1980 | Mack, Jr. et al. |

(Continued)

FOREIGN PATENT DOCUMENTS

| | | |
|---|---|---|
| CA | 2 557 996 | 9/2005 |
| CN | 86202005 U | 6/1987 |

(Continued)

OTHER PUBLICATIONS

International Search Report and Written Opinion of International Application No. PCT/US2009/64949 dated Jan. 13, 2010.

(Continued)

*Primary Examiner* — Christopher Adam Hixson
*Assistant Examiner* — Emily R. Berkeley
(74) *Attorney, Agent, or Firm* — Dugan & Dugan, PC

(57) ABSTRACT

A device and system for automatic handling of a sensor strip by a part of a meter that includes a sensor strip having a first section, a second section, and an intermediate section. The sensor strip includes at least a first opening about a first end thereof and a second opening about a second end thereof. A meter part includes a pair of pivoting catches configured to engage and grasp a sensor strip from a container containing a plurality of sensor strips. The sensor strip may thus be removed from a container for testing without need for manual handling of the strip by a user.

12 Claims, 13 Drawing Sheets

(56) References Cited

U.S. PATENT DOCUMENTS

| | | |
|---|---|---|
| 4,705,331 A | 11/1987 | Britton |
| 4,721,677 A | 1/1988 | Clark |
| 4,771,887 A | 9/1988 | Nehl |
| 5,314,825 A | 5/1994 | Weyrauch et al. |
| 5,335,816 A | 8/1994 | Kaufman et al. |
| 5,335,822 A | 8/1994 | Kasper |
| 5,375,920 A | 12/1994 | Macchi |
| 5,609,823 A | 3/1997 | Harttig et al. |
| 5,846,486 A | 12/1998 | Pugh |
| 5,854,074 A | 12/1998 | Charlton et al. |
| 5,856,195 A | 1/1999 | Charlton |
| 6,036,924 A | 3/2000 | Simmons |
| 6,099,802 A | 8/2000 | Pugh |
| 6,130,263 A | 10/2000 | Hekal |
| 6,136,352 A | 10/2000 | Silverstein et al. |
| 6,170,230 B1 | 1/2001 | Chudy et al. |
| 6,378,702 B1 | 4/2002 | Kintzig |
| 6,625,952 B1 | 9/2003 | Chudy et al. |
| 6,827,899 B2 | 12/2004 | Maisey |
| 6,881,578 B2 | 4/2005 | Otake |
| 6,908,008 B2 | 6/2005 | Pugh |
| 6,997,343 B2 | 2/2006 | May |
| 7,138,089 B2 | 11/2006 | Aitken |
| 7,264,139 B2 | 9/2007 | Brickwood et al. |
| 7,270,247 B2 | 9/2007 | Charlton |
| 7,501,093 B2 | 3/2009 | Demelo et al. |
| 7,552,843 B2 | 6/2009 | Kuriger et al. |
| 7,638,095 B2 | 12/2009 | Sabol |
| 7,723,113 B2 | 5/2010 | Charlton |
| 7,875,243 B2 | 1/2011 | Rush et al. |
| 8,236,254 B2 | 8/2012 | Myles et al. |
| 8,388,905 B2 | 3/2013 | Neel et al. |
| 8,684,172 B2 | 4/2014 | Yao |
| 8,691,161 B2 | 4/2014 | Fleming |
| 8,940,540 B2 | 1/2015 | Charlton et al. |
| 9,097,699 B2 | 8/2015 | Charlton et al. |
| 2002/0057993 A1 | 5/2002 | Maisey et al. |
| 2002/0076349 A1 | 6/2002 | Aitken et al. |
| 2003/0089730 A1 | 5/2003 | May et al. |
| 2003/0116583 A1 | 6/2003 | Pugh |
| 2003/0175155 A1 | 9/2003 | Charlton |
| 2003/0191415 A1 | 10/2003 | Moerman et al. |
| 2003/0211616 A1 | 11/2003 | Leong |
| 2003/0223906 A1 | 12/2003 | McAllister |
| 2004/0007585 A1 | 1/2004 | Griffith et al. |
| 2004/0178216 A1 | 9/2004 | Brickwood et al. |
| 2005/0142363 A1 | 6/2005 | Noda |
| 2006/0076236 A1 | 4/2006 | Shah et al. |
| 2006/0076358 A1 | 4/2006 | Shigeyama et al. |
| 2006/0191813 A1 | 8/2006 | Yamaoka |
| 2006/0266765 A1 | 11/2006 | Pugh |
| 2007/0125677 A1 | 6/2007 | Oronsky et al. |
| 2007/0183925 A1 | 8/2007 | Schabbach |
| 2007/0189928 A1 | 8/2007 | Sabol |
| 2007/0196240 A1 | 8/2007 | Boozer |
| 2007/0264165 A1 | 11/2007 | Chan et al. |
| 2008/0007141 A1 | 1/2008 | Deck |
| 2008/0094804 A1 | 4/2008 | Reynolds et al. |
| 2008/0108130 A1 | 5/2008 | Nakaminami et al. |
| 2008/0131322 A1 | 6/2008 | Kheiri |
| 2008/0164280 A1 | 7/2008 | Kuriger et al. |
| 2008/0181818 A1 | 7/2008 | Ruan |
| 2008/0257905 A1 | 10/2008 | Giraud et al. |
| 2008/0286149 A1 | 11/2008 | Roe et al. |
| 2009/0095071 A1 | 4/2009 | Wu et al. |
| 2010/0041156 A1 | 2/2010 | Brenneman et al. |
| 2011/0073476 A1 | 3/2011 | Gofman et al. |
| 2011/0226643 A1 | 9/2011 | Kates et al. |
| 2013/0324822 A1 | 12/2013 | Prais et al. |
| 2014/0054169 A1 | 2/2014 | Gofman et al. |
| 2014/0273041 A1 | 9/2014 | Charlton |
| 2015/0004059 A1 | 1/2015 | Brown et al. |
| 2016/0018385 A1 | 1/2016 | Sams et al. |

FOREIGN PATENT DOCUMENTS

| | | |
|---|---|---|
| CN | 1264854 A | 8/2000 |
| CN | 1651265 A | 8/2005 |
| CN | 101801268 | 8/2010 |
| JP | 2007-526464 | 9/2007 |
| TW | 200706850 | 2/2007 |
| TW | 200731955 | 9/2007 |
| WO | WO 2010/065307 | 6/2010 |
| WO | WO 2010/065309 | 6/2010 |
| WO | WO 2012-064645 | 5/2012 |
| WO | WO 2014/164705 | 10/2014 |

OTHER PUBLICATIONS

International Preliminary Report on Patentability of International Application No. PCT/US2009/64949 dated Jun. 16, 2011.

International Search Report and Written Opinion of International Application No. PCT/US2009/64963 dated Mar. 4, 2010.

International Preliminary Report on Patentability of International Application No. PCT/US2009/64963 dated Jun. 16, 2011.

International Search Report and Written Opinion of International Application No. PCT/US2014/023266 dated Jun. 16, 2014.

International Preliminary Report on Patentability of International Application No. PCT/US2014/023266 dated Sep. 24, 2015.

Taiwan Search Report of Taiwan Application No. 103108342 dated Jun. 1, 2015.

Taiwan Search Report of Taiwan Application No. 105105859 dated Aug. 15, 2016.

European Extended Search Report of European Application No. 14779994.4 dated Oct. 7, 2016.

Chinese Search Report of Chinese Application No. 201480013754.9 dated Apr. 18, 2017.

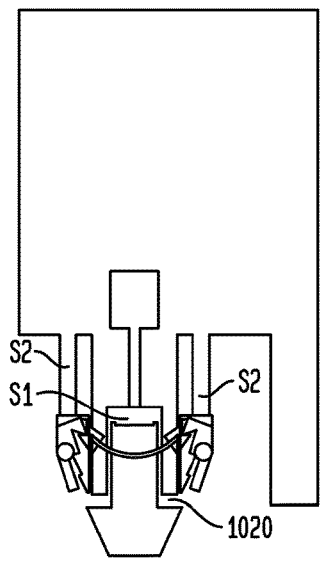
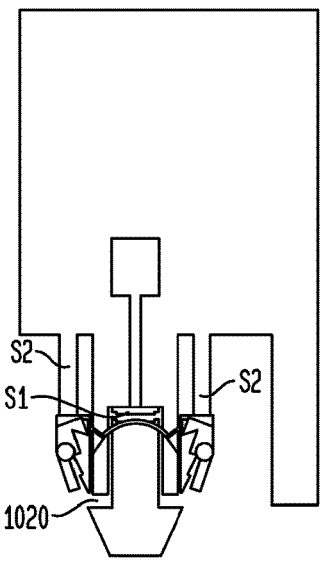
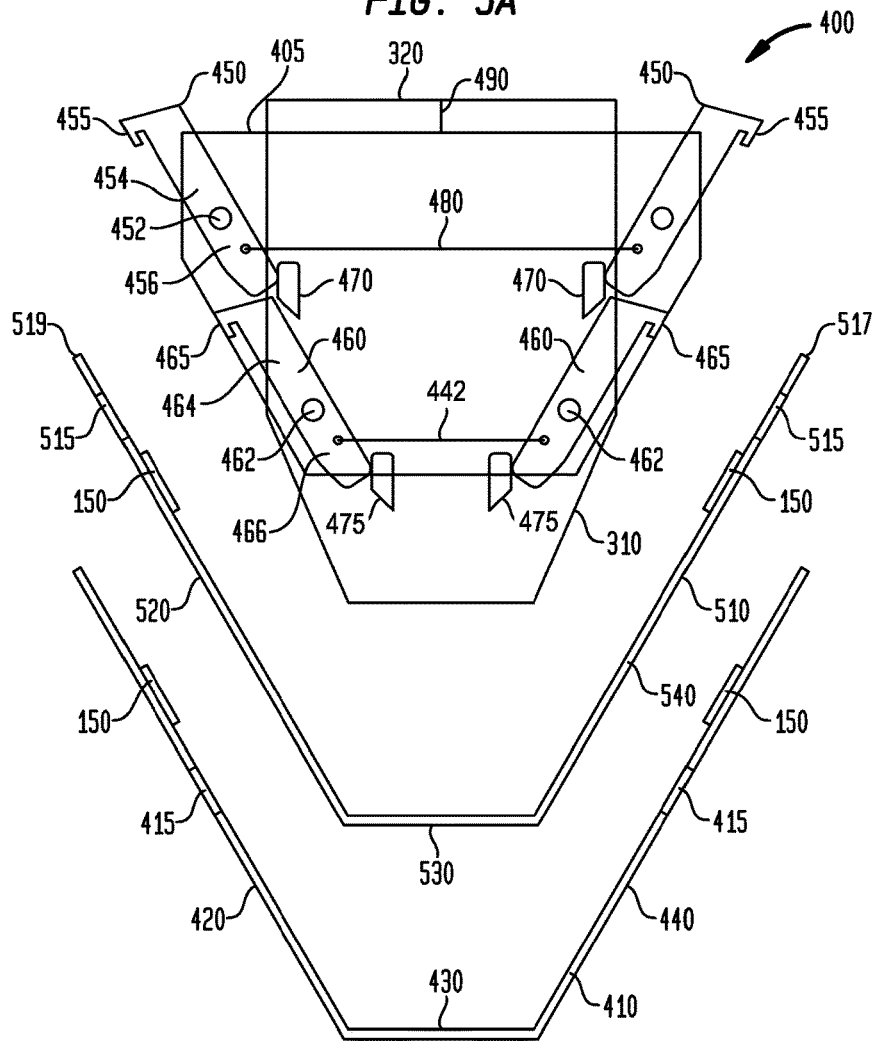

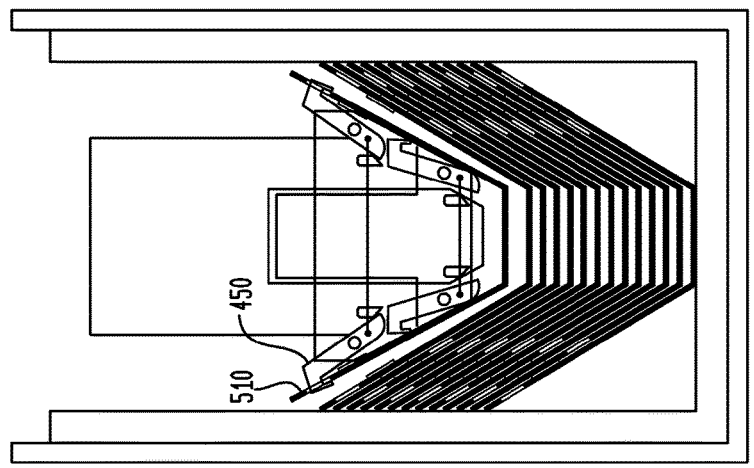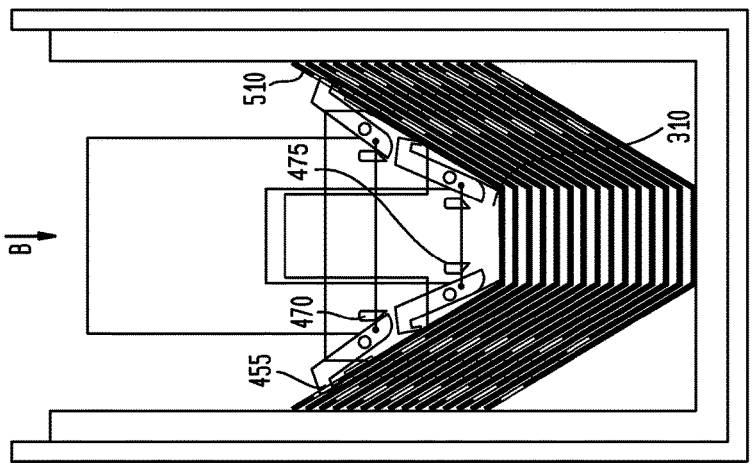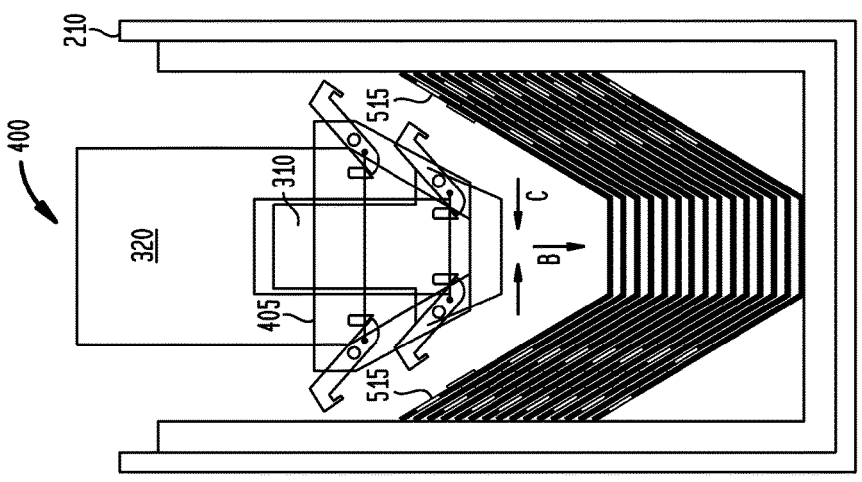

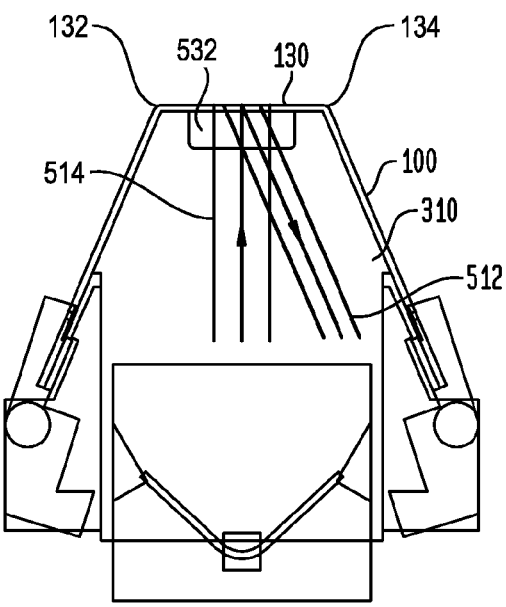
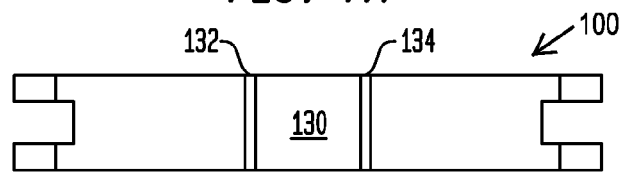
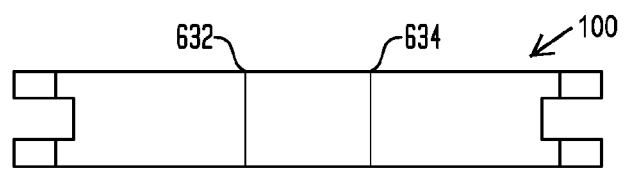
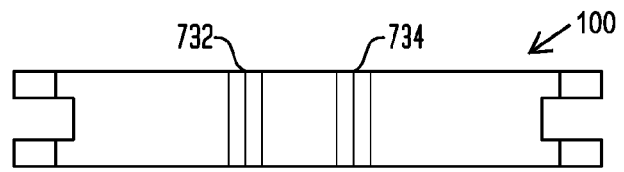
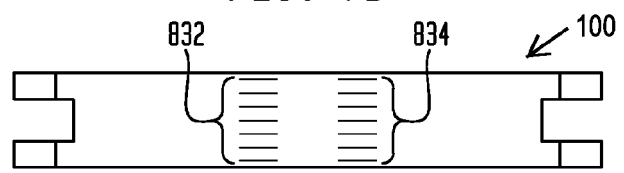

_US 10,132,791 B2_

BOTTLED GLUCOSE SENSOR WITH NO HANDLING

CROSS-REFERENCE TO RELATED APPLICATION

This is a division of U.S. patent application Ser. No. 13/800,799, filed Mar. 13, 2013, now U.S. Pat. No. 9,376,708, the disclosure of which is incorporated herein by reference in its entirety for all purposes.

FIELD OF INVENTION

The present invention is related to sensor strips for reading and handling diagnostic reagents and methods for using the same. More particularly, the present invention relates to sensor strips which may be stacked in a container and retrieved without manual handling of the same.

BACKGROUND OF THE INVENTION

The quantitative determination of analytes in body fluids is of great importance in the diagnoses and maintenance of certain physiological abnormalities. For example, lactate, fructosamine, cholesterol, bilirubin, alcohol, and drugs may be monitored or tested in certain individuals. The monitored or tested body fluids may include blood, interstitial fluid, saliva, or urine. In particular, determining glucose in body fluids is important to diabetic individuals who must frequently check the glucose level in their body fluids to regulate the glucose intake in their diets.

One method of monitoring or testing body fluids is with a portable, hand-held blood testing device. The portable nature of these devices enables the users to conveniently test their blood wherever the user may be. The testing device includes a biosensor to harvest the fluid sample for analysis. One type of biosensor is the electrochemical biosensor. The electrochemical biosensor includes a reagent designed to react with analytes in the fluid sample to create an oxidation current at electrodes disposed within the electrochemical biosensor which is directly promotional to the user's blood glucose concentration or analyte being detected. Such a biosensor is described in U.S. Pat. Nos. 5,120,420; 5,660,791; 5,759,364; and 5,798,031; each of which is incorporated herein in its entirety. Another type of sensor is an optical biosensor, which incorporates a reagent designed to produce a colorimetric reaction indicative of analytes in a user's blood or fluid sample. The calorimetric reaction is then read by a spectrometer incorporated into the testing device. Such an optical biosensor is described in U.S. Pat. No. 5,194,393, which is incorporated herein by reference in its entirety.

Biosensors in this "strip" form, i.e., test strips that include a reagent area on an elongated body, are generally inexpensive to produce. However, such sensors, and particularly optical sensors, are not conducive to optical testing because the read head of a meter that is required to analyze and read the sample requires protection from contamination by the sample. One solution to this problem is to wrap a sensor around the read-head so as to cover the read-head and prevent the sample from contacting the read-head. However, it is difficult to devise a method to remove such a sensor from a container without requiring intricate manipulations by a user. The average consumer is typically unwilling nor capable of intricate handling of such optical sensors and corresponding meters.

A need therefore exists for further improvements to sensors and methods for manufacturing sensors that require minimal costs and better handling of the sensors, as well as devices, systems, and methods for storing and handling sensors that are inexpensive and easy to use.

BRIEF SUMMARY OF THE INVENTION

In an exemplary embodiment of the invention, a sensor strip comprises an elongated body comprising a first section, an intermediate section, and a second section. The elongated body further comprises a first divider between the first section and the intermediate section and a second divider between the second section and the intermediate section. The first and second sections comprise a first and a second opening, respectively. The first and second sections comprise a first and a second raised section, respectively. The intermediate section is configured as a reagent section.

According to an embodiment of the invention, a meter for testing an analyte comprises a read-head configured for interrogating a reagent section of a sensor strip, a housing, a pair of stationary catches disposed along the housing, and a pair of pivoting catches pivotably mounted along the stationary catches. Each of the stationary catches comprises a surface defining first and second steps, respectively. Each of the pivoting catches comprises a lower arm, an upper arm and a pivot point disposed between the upper arm and the lower arm. Each of the lower arms comprises a surface generally complementing the surfaces of the stationary catches and first and second steps defined along the surfaces, respectively. The pivoting catches are configured such that a pivoting of the upper arms toward the housing causes the lower arms to pivot away from the stationary catches and a pivoting of the upper arms away from the housing causes the lower arms to pivot toward the stationary catches. The meter further comprises a body configured to selectively move in a longitudinal direction of the read-head away and toward the read-head. The relative movement of the housing and the read-head allows tensioning of the test strip about the read-head.

The body comprises first and second slots defined there within. First and second cam elements are pivotably coupled to the body. A bias element is configured to couple the first and second cam elements to one another such that the first and second cam elements extend away from the body. A release button is coupled to the bias element such that a first movement of the bias element causes the first and second cam elements to be retracted into the first and second slots, respectively. The first and second cam elements are configured, in a first position thereof, to urge the upper arms of the pivoting catches to pivot about the respective pivot points such that the lower arms pivot toward the stationary catches. The steps of the stationary and pivoting catches are configured to cooperatively engage a sensor strip there between.

According to an aspect of the invention, a meter for testing an analyte comprises a read-head configured for interrogating a reagent section of a sensor strip and a housing arranged about the read-head. The housing comprises first and second lower catches pivotably mounted on the housing, a first bias element coupling the first and second lower catches to one another, and first and second lower cam elements in engagement with the first and second catches. The housing further comprises first and second upper catches pivotably mounted on the housing, a second bias element coupling the first and second upper catches to one another, and first and second upper cam elements in engagement with the first and second upper catches. Each of the first and second upper catches and the first and second lower catches comprises a projection configured to engage an opening in a sensor strip. A third bias element is configured to activate the first and second upper cam elements and the first and second lower cam elements to pivot, respectively, the first and second upper catches and the first and second lower catches away from the housing.

According to an aspect of the invention, a method for removing a sensor strip from a container comprises inserting a meter portion comprising a pair of pivoting catches into the container containing at least one sensor strip comprising first and second openings and causing the pivoting catches to pivot toward the at least one sensor strip and engaging the further comprises catches via the first and second openings. The method further comprises grasping the sensor strip via the pivoting catches via the first and second openings engaged by the pivoting catches, thereby tensioning the sensor strip about a read-head of the meter portion. According to an aspect of the invention, the method comprises grasping the sensor strip between the pivoting catches and a pair of stationary catches arranged about the meter portion inserted into the container. According to another aspect of the invention, the method comprises engaging the first and second openings of the sensor strip via first and second hooks defined along the pivoting catches.

BRIEF DESCRIPTION OF THE DRAWINGS

Various embodiments of the present invention will now be discussed with reference to the appended drawings. It is to be appreciated that these drawings depict only some embodiments of the invention and are therefore not to be considered limiting of its scope.

FIG. 3AA schematically illustrates a cam element and a slot within a push button of the meter part of FIG. 3A, according to an embodiment of the invention;

FIGS. 4A-4E schematically illustrate different relative positions of the components of a meter with a meter part of FIG. 3A, including a release button, according to an embodiment of the invention;

FIG. 5A illustrates another embodiment of a meter portion configured to cooperate with another embodiment of an optical sensor strip;

FIGS. 5B-5D schematically illustrate different stages of retrieving a sensor strip of FIG. 5A from a container, according to the embodiment of FIG. 5A;

FIG. 6 schematically illustrates an optical sensor strip of FIG. 1A wrapped around a reading head of a meter of FIG. 2A;

FIG. 7A illustrates a top view of an optical sensor strip while FIGS. 7B-7D illustrate three different embodiments of the bottom view of the optical sensor strip of FIG. 7A, according to various embodiments of the invention;

DETAILED DESCRIPTION

Figure 1A:
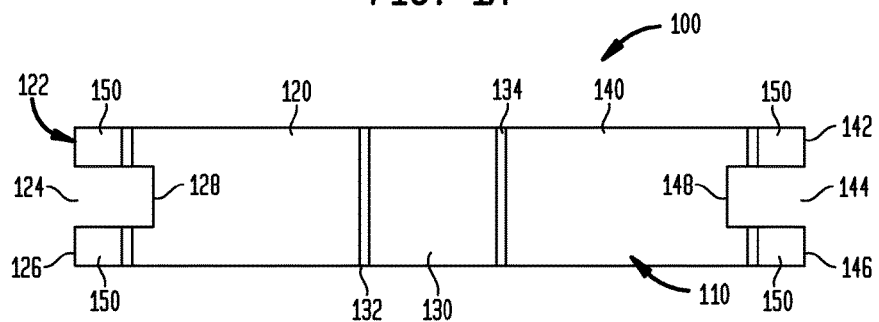
FIG. 1A is a top view of an optical sensor strip, according to an embodiment of the invention.

While the embodiments disclosed herein are susceptible to various modifications and alternative forms, specific embodiments thereof have been shown by way of example in the drawings and will herein be described in detail. It should be understood, however, that it is not intended to limit the invention to the particular forms disclosed but, on the contrary, the intention is to cover all modifications, equivalents, and alternatives falling within the spirit and scope of the invention as defined by the appended claims.

The presently disclosed embodiments are directed to sensor strips for reading and handling diagnostic reagents in a stackable form in a container and the methods for using the same. The diagnostic reagents may be independently selected to test one or more analytes such as glucose, lactate, fructosamine, cholesterol, bilirubin, alcohol and/or drugs. It is contemplated that other analytes may be tested using the sensor strips and the meters described herein. The body fluids to be tested may include blood, interstitial fluid, saliva, or urine. It is contemplated that other fluids may be tested using the devices and methods described herein. One commonly tested analyte is glucose in a whole blood sample.

Figure 1B:
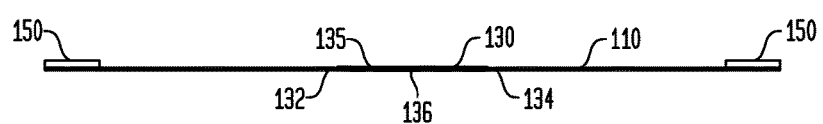
FIG. 1B is a front elevational view of the optical sensor strip of FIG. 1A.
Figure 1C:
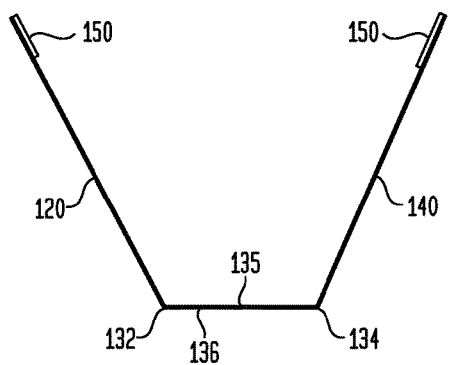
FIG. 1C is a front elevational view of the optical sensor strip of FIG. 1A in a bent configuration for storage.

Referring now to FIGS. 1A-1C, an optical sensor strip 100 is illustrated according to one embodiment. The strip 100 comprises a left section 120, an intermediate section 130, and a right section 140. The strip 100 further comprises a top surface 135 and a bottom surface 136. The intermediate section 130 and the left section 120 are delimited by a divider 132, whereas the intermediate section 130 and the right section 140 are delimited by a divider 134. In an exemplary embodiment, the dividers 132, 134 comprise a scribe line configured to permit bending of the sensor along the dividers 132, 134.

The intermediate section 130 comprises a reagent area. In one example, intermediate section 130 is the only section coated with an appropriate reagent. The type of reagents may depend on whether the test strip 100 is configured for optical interrogation or for electrochemical interrogation. For example, in an electrochemical test strip, the reagent area may include enzymes such as Glucose Oxidase, PQQ-Glucose Dehydrogenase, NAD-Glucose Dehyrodrogenase, and FAD-Glucose Dehydrogenase and mediators such as ferricyanide, 1,10-phenanthroline quinine, and osmium-based mediators. Other enzymes and mediators may of course be used based on the requirements of a given application. For an optical sensor, the reagent area may include glucose oxidase, peroxidase, and useful indicators for this reaction such as o-tolidine, tetramethylbenzidine, glucose dehydrogenase, hexokinase, glucose-6-phosphate dehydrogenase, NAD, diaphorase, phenazine methosulfate and useful indicators for this reaction such as 2-p-iodophenyl-3-p-nitrophenyl-5-phenyl and other tetrazoliums.

Reagent may be applied to the bottom surface 136 of the strip in the reagent area 130 between dividers 132, 134. It should be noted that the reference to a "top" surface refers to the surface facing a read-head of a meter and that reference to a "bottom" surface refers to the surface facing away from the read-head of the meter. Applying a reagent only along the reagent area reduces the amount of reagent consumed, thereby also decreasing the cost of production for the sensor strip 100.

The left section 120 and the right section 140 each have an aperture 124 and 144 positioned adjacent outermost edges of the test sensor 100, respectively. The aperture 124 defines first and second arms 122 and 126 adjacent outermost edge of the left section 120 and an inner edge 128. Likewise, the aperture 144 defines first and second arms 142, 146 adjacent outermost edge of the right section 140 and an inner edge 148. In the illustrated example, each of the arms 122, 126, 142, 146 comprises a raised section 150. For example, the raised section 150 may comprise lamination configured to have a top surface at an elevation relative to the sensor strip 120. When the sensor strips 100 are stacked, the raised section 150 can help minimize surface engagement between two adjacent sensor strips in the stack which otherwise may adversely affect the integrity of the strips. In one example, the raised section 150 minimizes contact between the respective reagent areas 130 on adjacent strips. The raised section 150 also facilitates greater ease with regard to handling and removal of a given sensor strip 150 from a container, as described in further detail below.

In one embodiment, the sensor strip 100 is made of a suitable material, for example, including but not limited to polyester, polycarbonate, and polystyrene. For example, a sensor strip may have a length of about 21 millimeters (mm) and a width of about 3.5 mm. According to an exemplary configuration, the reagent area 130 may have a length of about 4 mm and a width of about 3.5 mm. The apertures 124, 124 may have a length of about 2.1 mm and a width of about 1.6 mm. It will be understood that these dimensions are illustrative in nature and different dimensions may be employed given the requirements of a particular application.

FIG. 1C illustrates the sensor strip 100 in a bent configuration, wherein the left section 120 and the right section 140 are bent upward relative to the center section 130 along the dividers 132 and 134, respectively. As shown, both the left section 120 and right section 140 slope toward the center section 130. A plurality of sensor strips 100 may be stacked one upon another in a container in this bent configuration. In certain embodiments, the intermediate section 130 may further comprise a material to help distribute a fluid sample across the reagent area. For example, a mesh or a similar material (not shown) may cover the reagent area 130 to protect the reagent surface from abrasion during inoculation with the blood sample. Such a mesh (not shown) may further help in uniformly distributing the sample to the reagent area. The mesh or its equivalent (not shown) may be applied to the intermediate section 130 using a pressure-sensitive or heat-activated adhesive.

Figure 2A:
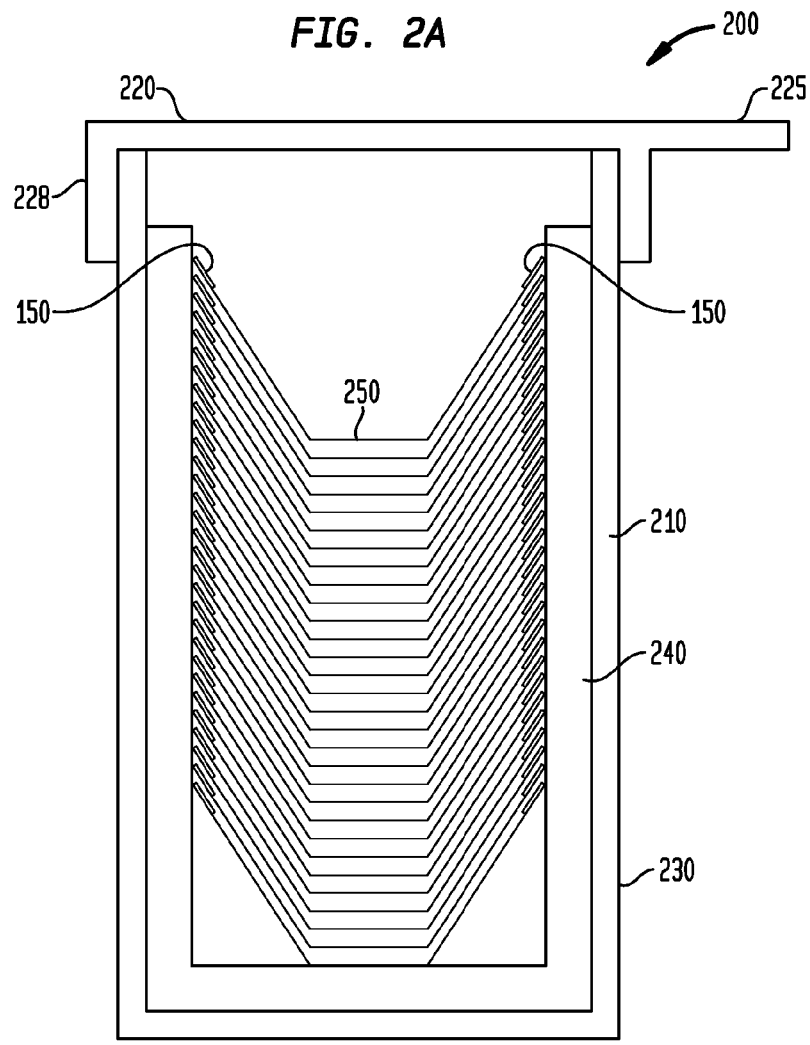
FIG. 2A is a front elevational view of a bottle containing a plurality of sensor strips of FIG. 1A, according to an embodiment of the invention.
Figure 2B:
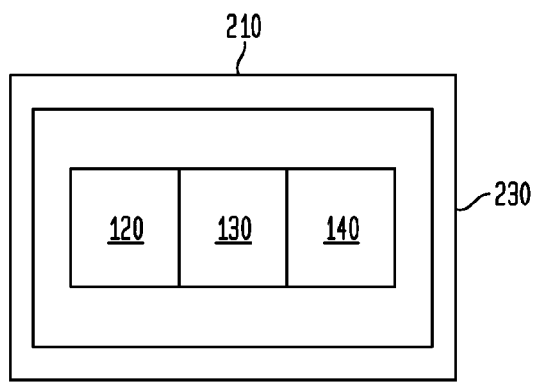
FIG. 2B is a top view of the bottle of FIG. 2A, without the lid.

Referring now to FIGS. 2A-2B, a container 200 for holding a plurality of sensor strips 100 is illustrated, according to an embodiment of the invention. The container 200 comprises a longitudinal body 210 having a generally rectangular cross-section. A desiccant 230 is lined along the interior of the body 210 for reducing moisture contamination of the sensor strips 100 stacked in the body. A lid 220 is configured to cover the body 210 in a generally air-tight manner. The lid 220 includes a projection 225 for facilitating the opening and closing of the lid 220. For example, the projection 225 is configured such that the lid 220 may be opened by a flick of a thumb. In one embodiment, the lid 220 may be hinged at one end 228 to body 210. In an alternative embodiment, the lid 220 may be completely removable from the body 210. The body 210 is dimensioned to accommodate a stack of sensor strips 100 in a bent configuration therein (as illustrated in FIG. 1C). The raised sections 150 of the sensor strip 100 create a gap 250 or space between the reagent areas 130 of two adjacent sensor strips. Such a gap 250 mitigates the risk of reagent contamination due to undesirable contact between a reagent area and a reverse side (top surface) of adjacent sensors strips.

Figure 3A:
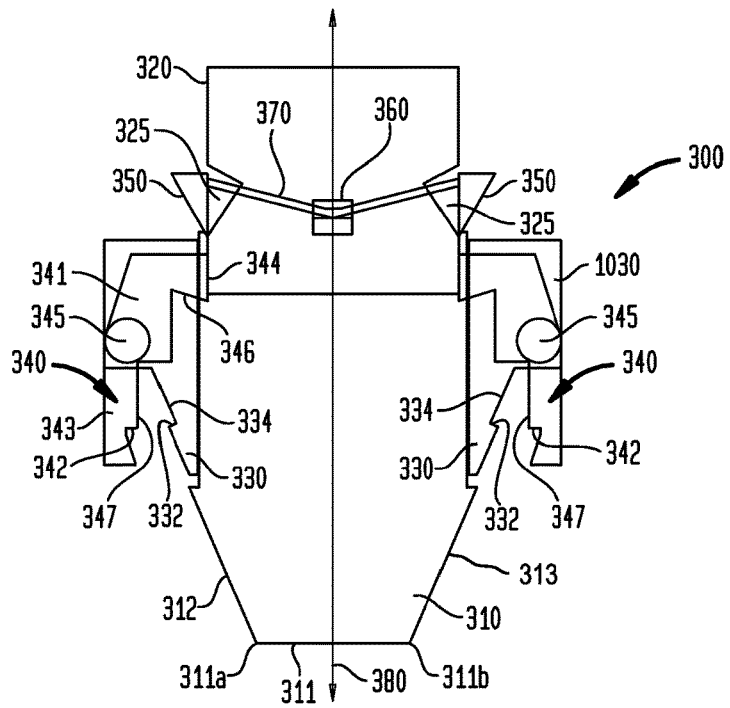
FIG. 3A schematically illustrates the meter part in a rest position before extracting a test strip from the bottle of FIG. 2A, according to an embodiment of the invention.
Figure 3A:
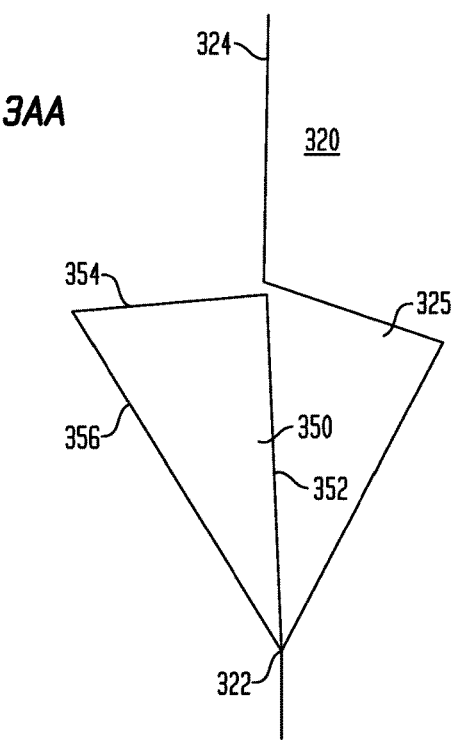

FIGS. 3A-3F, 3AA, and 4A-4E illustrate a meter part 300 configured to operate in conjunction with a sensor strip 100 according to one embodiment. The meter part 300 includes a read-head 310 and a housing 1030. The housing 1030 includes a pair 330 of stationary catches, a pair 340 of pivoting catches, a body 320 and a release button 360. The read-head 310 may be an optical read-head, which is known in the art and therefore is not described in further detail for the sake of brevity. In an alternative embodiment, the read-head 310 may comprise an electrochemical read-head, which is also known in the art and therefore is not described in further detail for the sake of brevity. The body 320 is configured to move relative to the read-head 310 along a longitudinal direction 380. Longitudinal direction 380 extends through a front portion 311 of the read-head and the body 320, as best shown in FIG. 3A. The left side 312 and right side 313 of the read-head 310 slope toward the front 311 of the read-head. The slope of the left sections 120 and the right section 140 in the bent configuration of the sensor strip 100 may be less than the slope of the left side 312 and right side 313 of the read-head 310.

The meter part 300 further comprises a pair of cam elements 350 coupled to one another via a bias element 370. In one embodiment, the bias element 370 may take the form of a flexible leaf of a metal, polyefin or other plastic. The body 320 may include slots 325 configured to receive and accommodate the cam elements 350 there within. The cam elements 350 may have a generally wedge-shaped configuration that includes a first surface 352, a second surface 354 and a third surface 356 (FIG. 3AA). The cam element 350 is configured to pivot about a pivot point 322 into and out of the slot 325. In a first position, the first surface 352 is generally coplanar with an outer surface 324 of the body 320, the second surface 354 is generally perpendicular to the outer surface 324, and the third surface 356 inclines away from outer surface 324. In the second position of the cam element 350, when accommodated within the slot 325, the third surface 356 is generally parallel to the outer surface 324. Movement of the release button 360 away from the read-head 310 pulls the bias element 370. As the bias element 370 is pulled by the release button 360, the cam elements 350 are pulled inward toward and ultimately into the respective slots 325. The bias element 370 is configured to maintain the cam elements 350 in the first position, extending away from the push button 360.

The pivoting catches 340 each comprises an upper arm 341 and a lower arm 343. The pivoting catches 340 are configured to pivot about their respective pivot points 345 towards and away from the stationary catches 330. A bias element (not shown), for example, a coil spring, is arranged about the pivot points 345 and is configured to push the upper arms 341 toward the body 320 and to push the lower arms 343 away from the body 320. The lower arms 343 of each of the stationary catches 330 comprise a generally tapered first surface 334 and a step 332 defined thereupon. Each of the pivoting catches 340 comprises a generally tapered second surface 347 and a step 342 defined thereupon. The generally tapered surfaces 334 are generally aligned with the tapered surfaces of the read-head 310. The generally tapered surfaces 347 are configured to complement the surfaces 334 when the lower arms 340 are pivoted toward the stationary catches 330. Likewise, the steps 342 are configured to generally complement the steps 332 when the lower arms 343 are pivoted toward the stationary catches 330. In an alternative embodiment, longitudinal surfaces of the read-head 310 and the mating surfaces 334, 347 of the rotating catches may be parallel to the outer edge 324 of the body 320.

The upper arms 341 of the pivoting catches have an inner surface 344 that is generally parallel to the outer edge 324 of the body 320 and a step surface 346 generally perpendicular to the outer edge 324 of the body 320. The steps 332, 342 are defined so that when the lower arms 343 of the pivoting catches 340 pivot toward the stationary catches 330, the steps 332, 342 align with one another. When the lower arms 343 of the pivoting catches 340 pivot toward the stationary catches 330, the upper arms 341, including the inner surfaces 344, move away from the push button 360, urged by the cam elements 350, as described in detail below. The stationary catches 330 and the pivoting catches 340 are generally constrained to the read-head 310, while the push button 360 is configured to move toward and away from the read-head 310.

Figure 4A:
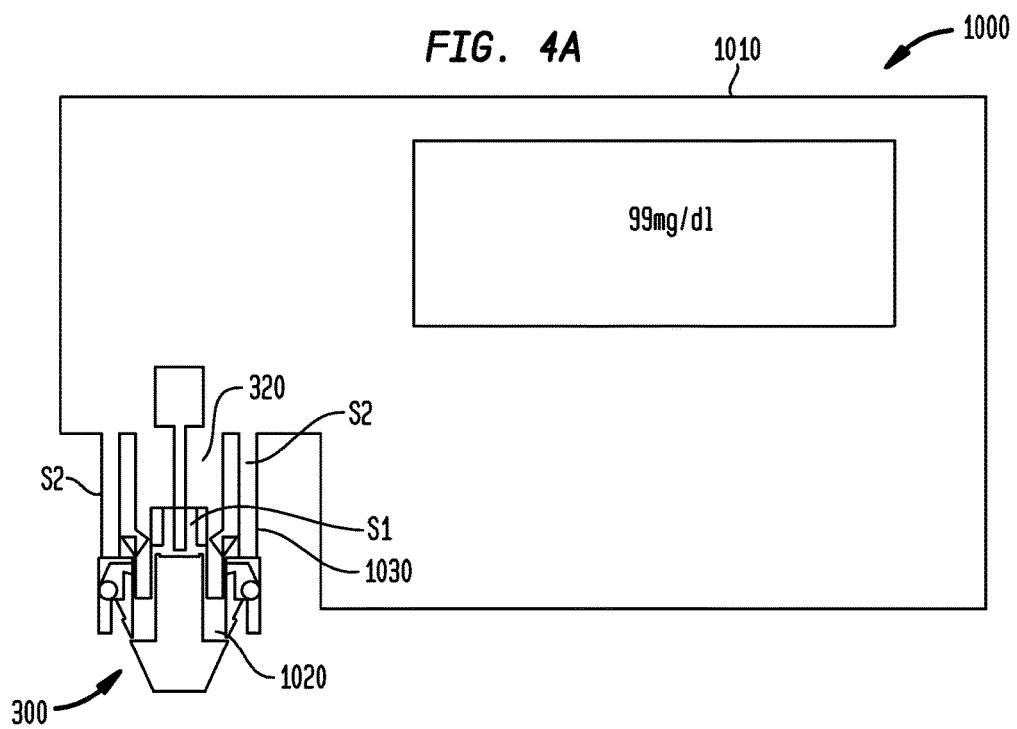
Figure 4B:
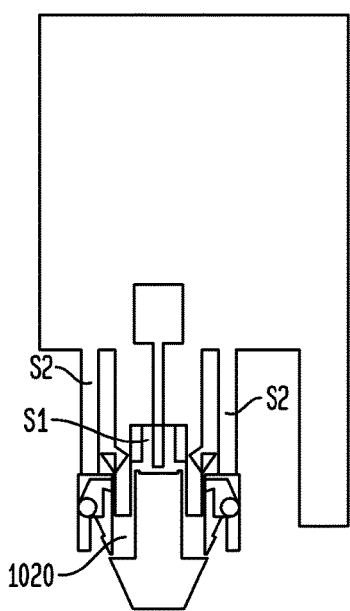
Figure 4C:
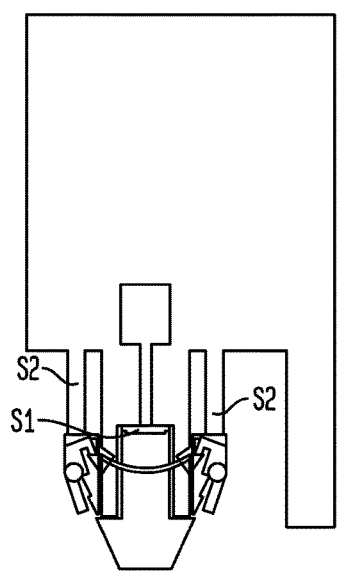

FIGS. 4A-4C illustrate biasing of the read-head 310 of a meter. In this example, read-head 310 may be biased by a spring S1 away from the body 320 of the meter 1000 to leave a gap 1020 between the read-head 310 and the housing 1030. The housing 1030, in turn, is biased away from the body 320 by at least one spring S2. Springs S1 and S2 are configured such that downward movement of the body 320 along the longitudinal axis 380 (FIG. 3A) initially compresses spring S1, closing the gap 1020 between read-head 310 and housing 1030 (FIG. 4C). Further downward movement of the body 320 compresses the springs S2 allowing the body 320 to move towards the housing 1030 (FIG. 4C).

Referring back to FIG. 3C, the meter part 300 may be inserted into a container 200 containing a plurality of sensor strips 100. The meter part 300 may be inserted into the body 210 to a depth that is generally sufficient for the read-head 310 to be proximal to and in an initial gentle contact, i.e., without applying any significant pressure, with the intermediate section 130 of the topmost sensor strip 100. As the meter part 300 is pushed into the body 210, the read-head 310 retracts relative to the body 320 under a spring pressure of the spring S1. The lower arms 343 of the pivoting catches 340 are accommodated in the apertures 124, 144 of the stack of the sensor strips 100 in the body 210. The steps 342 are configured on the pivoting catches 340 so as to engage the inner edges 128, 148 of the topmost sensor strip 100. The depth of the steps 342 may be generally equal to the height of the raised section 150 of the sensor strip 100 illustrated in FIGS. 1C and 3C. In one embodiment, when the meter part 300 is inserted into a container comprising a plurality of sensor strips 100, one and only one sensor strip, i.e., the topmost sensor strip or the sensor at the top of the stack, is engaged by the meter part 300.

Figure 3B:
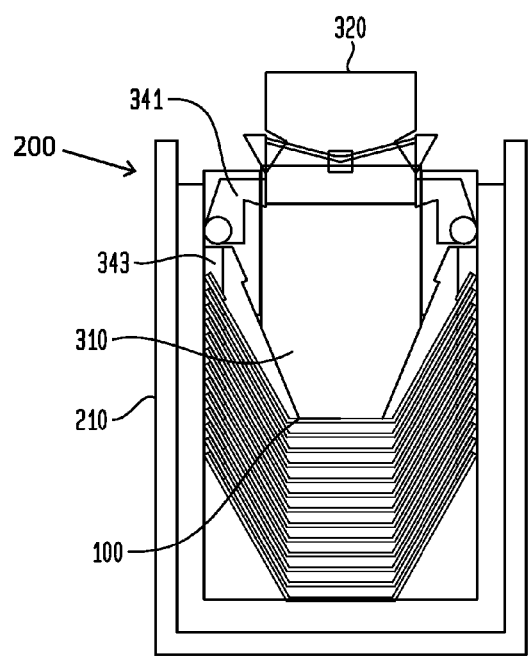
FIG. 3B schematically illustrates the relative position of the components of the meter portion of FIG. 3A inserted into a bottle of FIG. 2A and in a first contact with the topmost sensor strip, according to an embodiment of the invention.
Figure 3C:
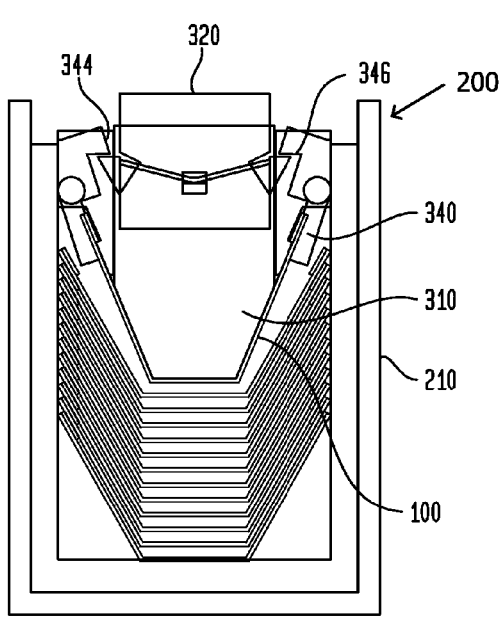
FIG. 3C schematically illustrates the relative positions of the components of the meter portion of FIG. 3A fully inserted into the bottle and in the process of grasping the sensor strip of FIG. 1A with the sensor strip loosely wrapped about a read-head of the meter portion, according to an embodiment of the invention.
Figure 3D:
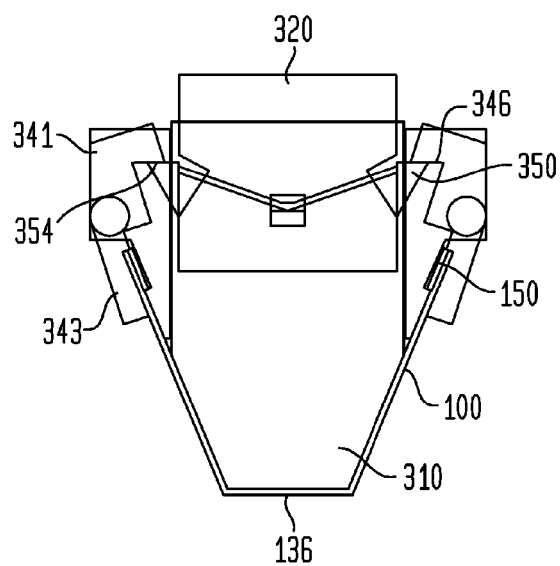
FIG. 3D illustrates the relative positions of the components of the meter portion of FIG. 3A with a sensor strip wrapped tightly about the read-head and removed from the bottle of FIG. 2A.

FIG. 3D illustrates one embodiment of a topmost sensor strip 100 being removed from the body 210. More particularly, once the read-head 310 has been inserted into the body 210 and the lower arms 343 of the pivoting catches 340 have established contact with the topmost sensor strip 100, the body 320 may be pushed toward the read-head 310. As the body 320 moves toward the read-head 310, the inner surfaces 344 of the upper arms 341 of the pivoting catches 340 engage the third surfaces 356 (FIG. 3AA) of the cam elements 350. Further movement of the body 320 toward the read-head 310 against the spring pressure of the springs S2 (FIG. 4C) causes the inner surfaces 344 and the upper arms 341 of the pivoting catches 340 to pivot away from the body 320, while the lower arms 341 pivot toward the body 320 along with the topmost sensor strip 100. As the body 320 is pushed further toward the read-head 310, the step surfaces 346 of the pivoting catches 340 engage the second surfaces 354 of the cam elements 350, thereby locking the upper arms 341 of the pivoting catches away from the body.

Figure 3E:
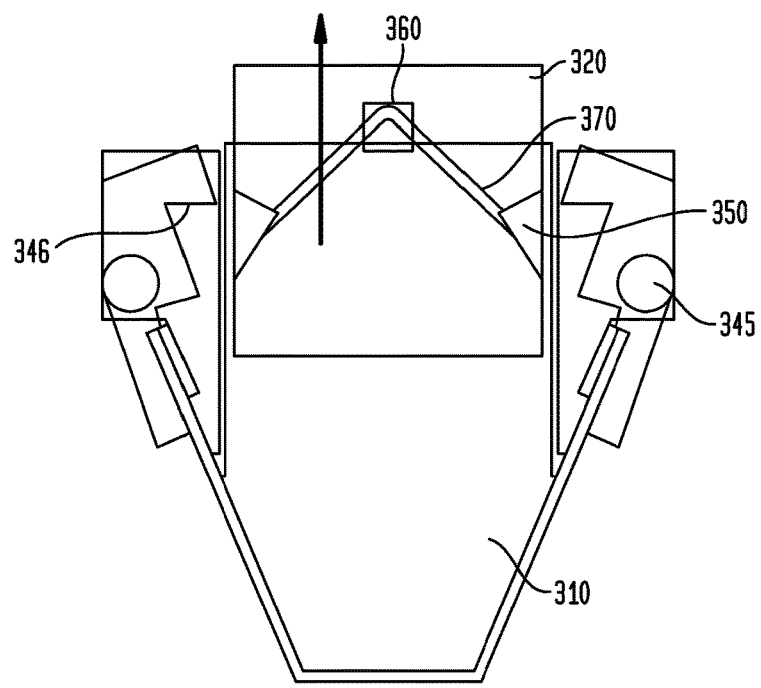
FIG. 3E illustrates the relative positions of the components of the meter portion of FIG. 3D returning to their rest positions in the process of releasing the sensor strip.

On the other end, the topmost sensor strip 100 is pushed against the stationary catches 330 such that the raised section 150 engages with the step 332 and is held thereon, grasped between the steps 342 of the pivoting catches 340 and the steps 332 of the stationary catches 330. The meter part 300 may then be pulled out of the body 210 along with the topmost sensor strip 100, as illustrated in FIG. 3E. The pressure of the spring S1 biases or pushes the read-head 310 toward the sensor strip 100, thereby introducing tension in the sensor strip 100 and preparing the sensor strip 100 for receiving a blood sample. The sensor strip 100 is wrapped around the meter part 300 under tension (FIG. 3D), and in particular the read-head 310, thereby protecting read-head 310 from contamination by the sample. The described configuration is user friendly and permits a user to extract a sensor from a container without having to handle or manipulate the sensor. A user may invert the meter part 300 and deposit, for example, a blood sample upon the bottom surface 136 that contains a reagent for testing. In general, tension in the sensor strip 100 may be generated by a relative movement between the read-head 310 and the housing 1030 wherein the read-head 310 may be fixed relative to the body 320, while a part of the meter body including the body may move relative to read-head 310.

Figure 3F:
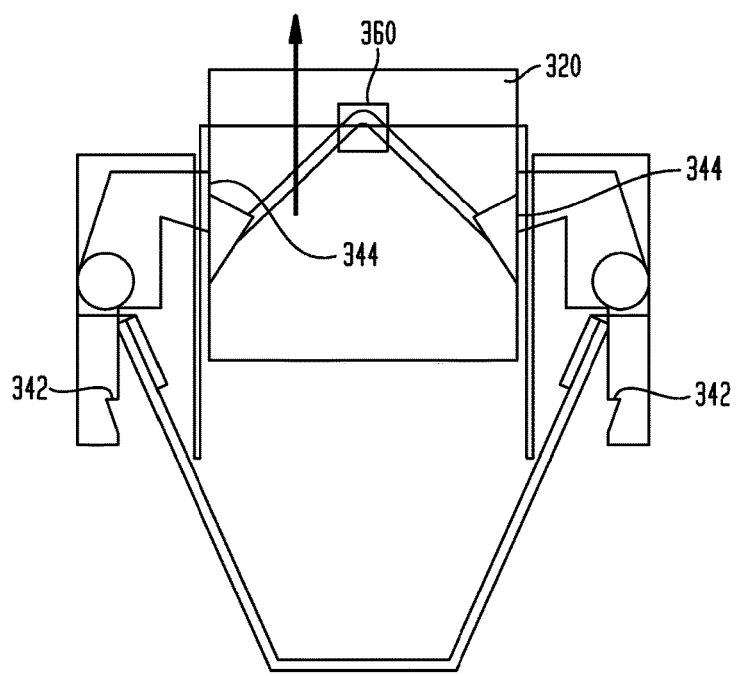
FIG. 3F illustrates the sensor strip of FIG. 1A being released from the meter portion of FIG. 3A, according to an embodiment of the invention.

After completing a test, the user may push the release button 360 in a direction away from the read-head 310 as illustrated in FIG. 3F by an arrow A. The release button 360 in turn pulls the bias element 370 in the direction away from the read-head 310 shown by the arrow A, thereby pulling the cam elements 350 inward into the slots 325 in the body 320. The movement of the cam elements 350 into the slots 325 releases the step surfaces 348 of the pivoting catches 340.

The release of the step surfaces 346 in turn causes the upper arms 341 of the pivoting catches 340 to pivot about the pivot point 345 such that the upper arms 341 move toward read-head 310 while the lower arms 343 move away from the stationary catches 330. The movement of the lower arms 343 away from the stationary catches 330 releases the sensor strip grasped there between, which may now be discarded.

Referring now to FIG. 5A, alternative embodiments of sensor strips 410, 510, as well as meter part 400 for accommodating sensor strips 410, 510 are illustrated. Each of the left sections 420, 520 of the respective sensor strips 410, 510 and each of the right sections 440, 540 of the respective sensor strips 410, 510 comprises a raised section 150. The sensor strips 410, 510 do not have the slots such as apertures 124, 144 defined in the sensor strip 100 (FIG. 1A). Instead, the sensor strips 410, 510 have openings 415, 515 defined there within as illustrated. More particularly, in the sensor strip 410, a first opening 415 is defined in the left section 420 between the raised section 150 and the intermediate section 430 and a second opening 415 is defined in the right section 440 between the raised section 150 and the intermediate section 430. In the sensor strip 510, on the other hand, a first opening 515 is defined between an edge 519 of the left section 520 and the raised section 150 and a section opening 515 is defined between an edge 517 of the right section 540 and the raised section 150.

A container may contain a plurality of sensor strips, wherein the sensor strips 410, 510 are disposed alternately, i.e., a sensor strip 510 is disposed upon a sensor strip 410, whereupon another sensor strip 510 is disposed. Such an arrangement ensures the openings 515, 415 of the alternating sensor strips 410, 510 are staggered and do not align with one another.

In an alternative embodiment, a sensor strip may comprise a first opening between an edge of a section and the raised section 150 on one side, for example, on a left section, such as for example in the sensor strip 510, and a second opening between the intermediate section 530 and the raised section 150 on another side, for example, on a right section, such as for example in the sensor strip 410. In this instance, a plurality of sensor strips may be stacked so that none of the first openings, for example, on the left section align with an opening on the left section of the sensor strip immediately beneath it and none of the second openings, for example, on the right section align with an opening on the right section of the sensor strip immediately beneath it.

Still referring to FIG. 5A, the meter part 400 according to the illustrated embodiment includes a meter body 320, read-head 310 and a housing 405. Meter part 400 includes a set of lower cams 475 and a set of upper cams 470. The housing 405 further includes a set of lower catches 460 and a set of upper catches 450. The housing 405 further comprises a lower bias element 442 coupling the set of lower catches 460 to one another, an upper bias element 480 coupling the set of upper catches 450 to one another, and a third bias element 490 coupling the meter body 400 and the read-head 310. Each of the upper catches 450 comprises an upper arm 454 and a lower arm 456. Likewise, each of the lower catches 460 comprises an upper arm 464 and a lower arm 466. Each of the upper arms 454 of the upper catches 450 comprises a hook 455 and each of the upper arms 464 of the lower catches 460 comprises a hook 465.

Each of the lower arms 456 of the upper catches 450 is coupled to the other by the upper bias element 480. Each of the lower arms 466 is coupled to the other by the lower bias element 442. The third bias element 490 is configured to be activated when there is a relative movement between the meter body 320 and the read-head 310. The approach of the housing 405 to meter body 320 brings the upper cams 470 into contact with lower arms 456 of upper catches 450, thereby rotating the upper catches 450 to cause the movement of the lower arms 456 outward away from the housing 405 and upper arms 454 inward towards the housing. Similarly, the contact of the lower cams 475 with the lower catches 460 causes the upper arms 464 of the lower catches to move inward towards the housing 405.

Referring now to FIGS. 5B-5D, retrieval of a sensor strip from a container comprising a plurality of alternating strips 410, 510 using a meter part 400 is illustrated. In an initial rest position, both sets of catches 450, 460 are extended from the meter body 400 (for example, via the biasing elements, e.g., tension springs, 442, 480 respectively) in contact with the corresponding sets of cams 475, 470. An inward movement of the meter body 400 in the direction of the arrow B results in contact of both sets of upper arms 454, 464 with the topmost sensor 510. In the embodiment illustrated in FIG. 5D, the projections 455 of the upper catches 450 engage the openings 515 of the topmost sensor strip 510. The upper set of catches 450 align with the sensor strip openings 515 allowing the upper arms 454 with the hooks 455 to engage the complementary sensor strip openings.

In contrast, the lower set of catches 460 in FIG. 5C meet only a solid surface between the raised sections 150 and the intermediate sections 430 and therefore are forced inward towards the meter body 400. If the topmost strip were sensor strip 410, the hooks 465 of the lower catches would engage the openings 415. It should be noted that since the sensor strip 410 beneath the sensor strip 510 does not have corresponding openings 515, the upper catches 450 can only engage the topmost sensor strip 510 in the illustrated embodiment. Further downward movement of the meter body 320 along the direction of the arrow B pushes the upper catches 450 downward ensuring capture of the sensor strip 510 by the hooks 455 as illustrated in FIGS. 5C and 5D. The read-head 310 retracts towards the meter body on first gentle contact with the topmost sensor and further downward movement of the meter body 320 relative to the housing 405 causes the cams 475, 470 of the body to engage the lower arms 466, 456 of the catches 460, 450, respectively, thereby pivoting the catches 450 with the grasped sensor sections 520, 540 toward the meter body 320. A latching mechanism (not shown) similar to the one activated by the release button 360 (FIG. 3A) locks the body 320 and the housing 405 together to maintain attachment of the sensor strip 510 to the read-head. As meter part 400 is removed from the longitudinal body 210, motion of the read-head 320 away from body 320 driven by third bias element 490 tensions the sensor strip 510. With the meter body 320 completely withdrawn from the longitudinal body 210 a user may now deposit a blood sample on the sensor strip 510. With the test complete, releasing the latch (not shown) via a release button (not shown, but similar to release button 360) causes relative movement of the meter body 320 and housing 405, the catches 450 to swing outward and the sensor strip 510 to be released and discarded.

Referring now to FIG. 6, an optical read-head 310 is illustrated according to an embodiment. The incident light beams 514 emanate from the read-head 310 and impinge upon the reagent section 130 of the sensor strip 100 mounted on the read-head 310, for example, as described above. The reflected light beams 512 are received within the read-head 310 for an analysis thereof. FIG. 6 illustrates a gap 532 defined between an optical element (not shown) of the read-head 310 and the reagent section 130. The gap 532 reduces the possibility of contamination of the optical element of the read-head 310 due to the reagent or the sample deposited on the sensor strip 100. When a sensor strip 100 is wrapped about or mounted to the read-head 310, the strip bends about the dividers 132, 134 to generally align the side-walls of the read-head. The intermediate section 130 between the dividers 132, 134 is configured to align with the gap 532 to allow impingement and reflection of the light beams 514, 512 from the read-head 310.

The intermediate section 130 lays flat across the read-head 310 to maintain uniformity and consistency of gap 532 which is made possible when the score and bend-lines 132, 134 (FIG. 7A) accurately align with the read-head corners 311a, 311b (FIG. 3A). Exemplary embodiments to mitigate a possible misalignment of the bend areas 132, 134 are illustrated in FIGS. 7B-7D. In FIG. 7B, score lines 632, 634 run across the short axis of the sensor strip 100. In FIG. 7C, multiple score lines 732, 734 run across the short axis of the sensor strip 100 and in FIG. 7D the lines 832, 834 are parallel to the longitudinal axis of the sensor strip 100. In both these cases, the pattern of lines 732, 734, 832, and 834 are generally centered about the nominal bend position 132, 134 with the intent of weakening the strip material, allowing the sensor strip 100 to conform to the meter corners 311a, 311b.

Figure 8A:
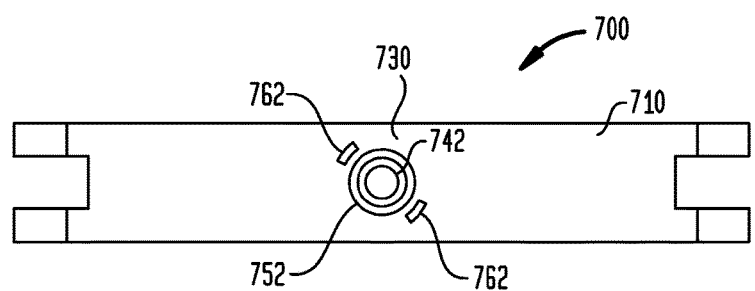
FIG. 8A illustrates a sample face of an electrochemical sensor strip, according to an embodiment of the invention.
Figure 8B:
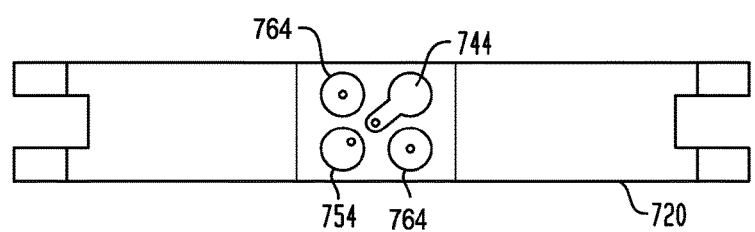
FIG. 8B illustrates a meter face of the electrochemical sensor strip of FIG. 8A, according to an embodiment of the invention.

Referring now to FIGS. 8A and 8B, an electrochemical sensor strip 700 is illustrated, according to an embodiment of the invention. The sensor strip 700 comprises a first face 710 configured to receive a sample and a second face 720 configured to face the meter. The sensor strip 700 is generally similar to the sensor strip 100 (FIG. 1A), except that the intermediate section 730 is configured to be interrogated electrically instead of optically as is the case for the sensor strip 100. The intermediate section 730 comprises a working electrode 742 and a counter electrode 752 disposed on the first face 710. Both the electrodes 742, 752 are covered with a reagent chemistry which may include an enzyme that specifically reacts with the desired analyte to reduce a mediator species. Electrons are transferred from the working electrode 742 to the reduced mediator in an oxidation reaction while at the counter electrode 752 electrons are transferred to the excess mediator or other species in a reduction process. These coupled reactions produce a flow of current in the external working electrode—counter electrode circuit. Relative areas of working and counter electrodes and other conditions are configured such that the measured current is limited and determined by re-oxidation of the mediator at the working electrode 742, consequently the measured current is representative of the analyte concentration.

Additional electrodes 762 may be included that allow measurement of electrical parameters such as current, resistance, capacitance to other electrodes. Such measurements may be useful for determining interfering species concentrations. The placement of the additional electrodes 762 with respect to the working electrode 742 and the counter electrode 752 may provide additional information related to the time at which sample solution was applied, whether sufficient sample solution was applied, sample flowrate, which may be related to the hematocrit. All this information may be useful in improving accuracy of the analyte concentration measurement. The surfaces of working and counter electrodes 742, 752 are configured to rapidly transfer electrons to and from the mediator, non-limiting examples being carbon, ferrocene and its derivatives, and the noble metals, gold, platinum and palladium. These electrodes may be defined on a substrate such as polyester or polycarbonate by an addition method such as screen printing or a subtraction method such as selective removal of a conductive noble metal coating.

The second face 720, on the other hand, comprises a contact pad 744 in electrical communication with the working electrode 742, a contact pad 754 in electrical communication with the counter electrode 752, and contact pads 764 in electrical communication with the under-fill detection and/or correction electrodes 762. An electrical read-head may contact the contact pads 744, 754, 764, on the center section 730 to receive, for example, an electric current representative of the extent of reagent reaction, for example, quantifying the detection of the desired analyte, from the underlying electrodes 742, 752, 762. In an alternative embodiment of the invention, the electrodes may be disposed on the face 710 configured for receiving the sample, thereby dispensing the need for the contact pads. The contact pads 744, 754, 764 may be electrically connected to the electrodes 742, 752, 762, respectively, via Vertical Interconnect Access (VIAs) or via Plated Through Holes (PTHs) in an exemplary embodiment of the invention. Since VIAs and PTHs are known in the art, they are not described in further detail for the sake of brevity.

Figure 9A:
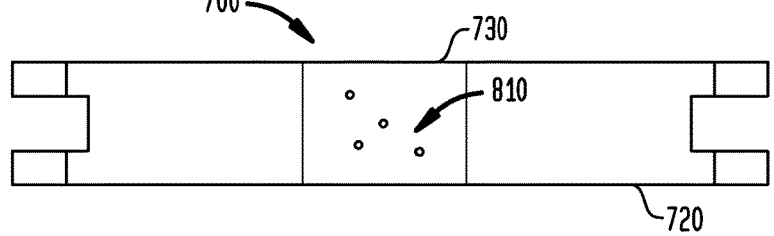
FIGS. 9A-9F illustrate various stages of a method for manufacturing an electrochemical sensor of FIGS. 8A-8B, according to an aspect of the invention.
Figure 9B:
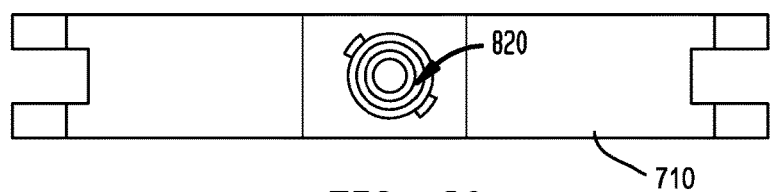
Figure 9C:
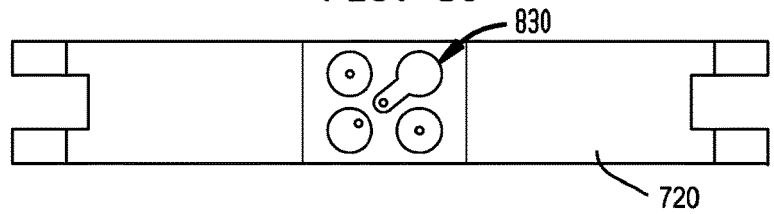
Figure 9D:
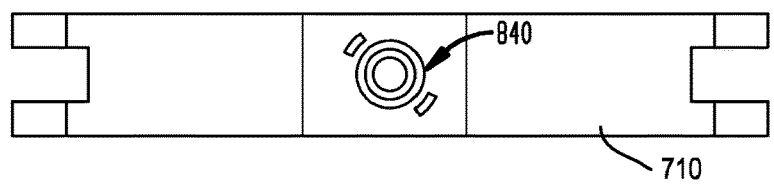
Figure 9E:
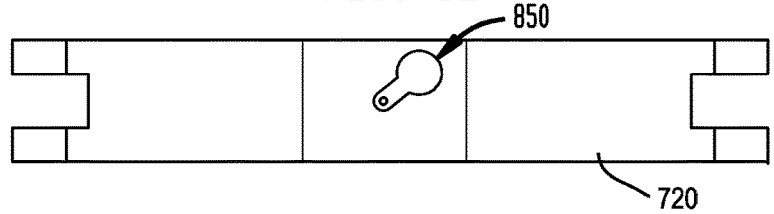
Figure 9F:
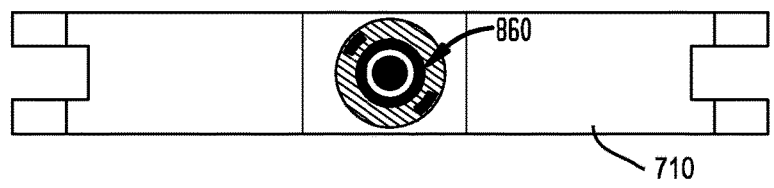

Referring now to FIGS. 9A-9F, a method for manufacturing a sensor strip 700 is described. FIG. 9A illustrates formation of through holes 810 in the center section 730. FIG. 9B illustrates the printing of an electrode pattern 820 on the face 710 of the sensor strip 700. FIG. 9C illustrates the printing of the contact pad pattern 830 on the face 720 of the sensor strip 700. FIG. 9D illustrates plating the electrodes 840 on the face 710 while FIG. 9E illustrates plating the contact pads 850 on the face 720. In FIG. 9F, the predetermined reagents may be coated on the face 710 of the sensor strip 700.

Figure 10A:
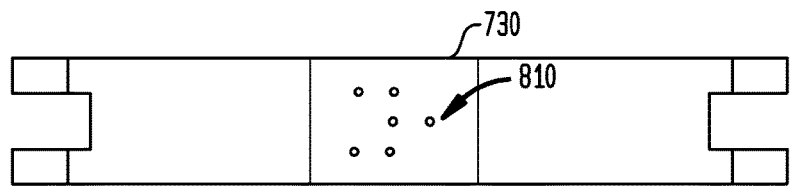
FIGS. 10A-10E illustrate various stages of another method for manufacturing an electrochemical sensor of FIGS. 8A-8B, according to an aspect of the invention.
Figure 10B:
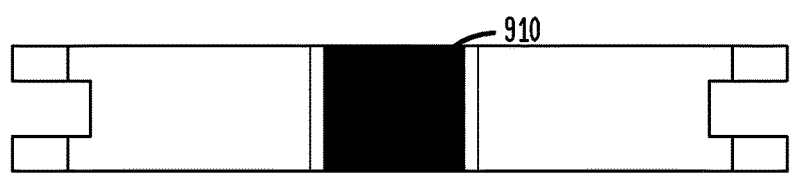
Figure 10C:
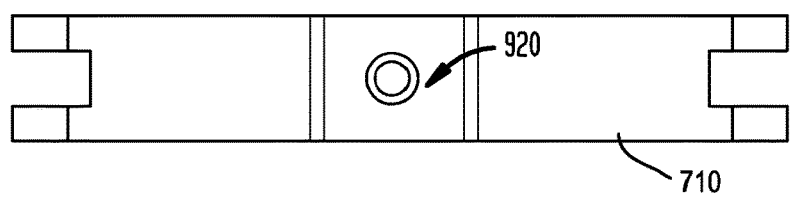
Figure 10D:
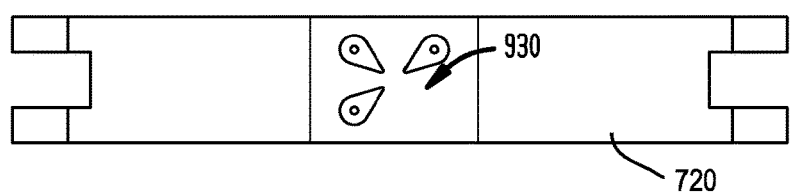
Figure 10E:
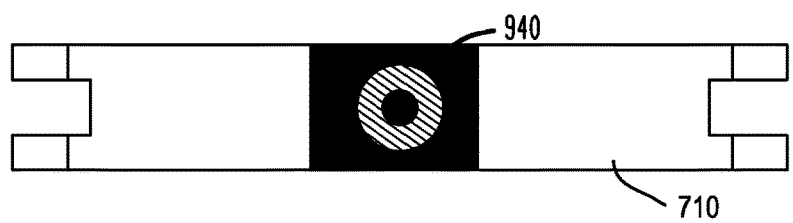

FIGS. 10A-10E illustrate another method for manufacturing a sensor strip 700. FIG. 10A illustrates formation of through holes 810 in the center section 730. FIG. 10B illustrates coating 910 on both faces 710, 720 along the center section 730, for example, by electroplating. FIG. 10C illustrates cutting an electrode pattern 920 in the coating 910 on the face 710 whereas FIG. 10D illustrates cutting a contact pad pattern 930 on the face 720. FIG. 10E illustrates application of a predetermined reagent 940 on the face 710.

Figure 11:
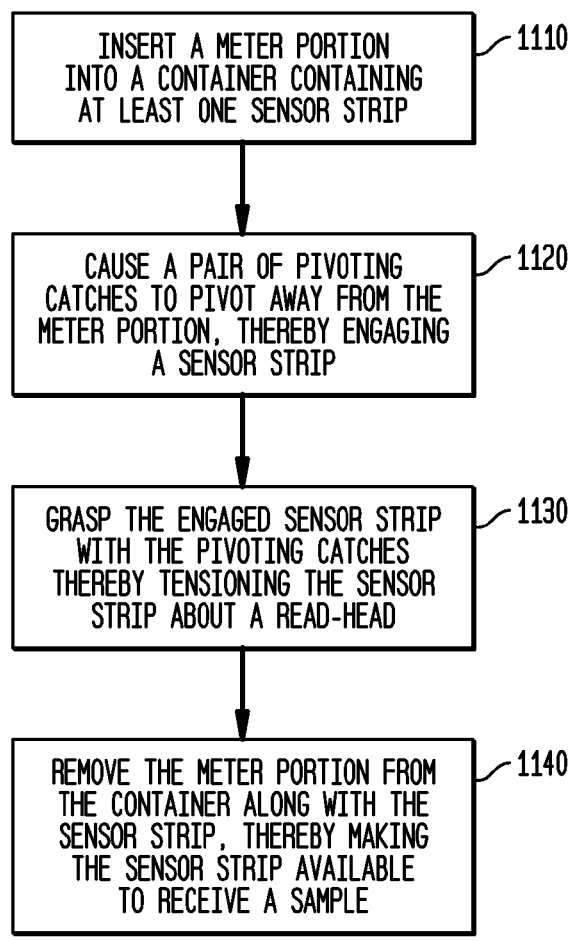
FIG. 11 illustrates a flow chart for a method for retrieving a sensor strip from a container, according to an aspect of the invention.

Referring now to FIG. 11, a flow diagram for a method for retrieving a sensor strip from a container is illustrated, according to an aspect of the invention. At block 1110, a meter portion (300; FIG. 3A) comprising a pair of pivoting catches (340; FIG. 3A or 450, 460; FIG. 5A) is inserted into a container (200) containing at least one sensor strip (100; FIG. 3B or 510, 410; FIG. 5A) comprising first and second openings (124, 144; FIG. 1A or 515 or 415; FIG. 5A). At block 1120, the pivoting catches are caused to pivot toward the at least one sensor strip and to engage the first and second openings. At block 1130, the sensor strip is grasped via the pivoting catches along the first and second openings, thereby tensioning the sensor strip about a read-head of the meter portion. At block 1140, the meter part is removed from the container along with the grasped sensor strip, thereby making the sensor strip available to receive a sample.

It will be appreciated that various features set forth in the embodiments discussed herein can be combined in different ways then presented herein. It will also be appreciated that the features described in connection with individual embodiments may be shared with other embodiments discussed herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as detailed by the following claims.

What is claimed is:

1. A method for retrieving a sensor strip from a container using a meter, the method comprising:
   inserting a meter portion comprising a pair of pivoting catches into the container containing at least one sensor strip comprising first and second openings;
   causing the pair of pivoting catches to pivot toward the at least one sensor strip and to respectively engage the first and second openings; and
   grasping the at least one sensor strip via the pair of pivoting catches at the first and second openings, wherein a read-head of the meter portion is tensioned about the at least one sensor strip.

2. The method of claim 1, wherein the grasping the at least one sensor strip comprises grasping the at least one sensor strip between the pair of pivoting catches and a respective pair of stationary catches arranged about the meter portion.

3. The method of claim 1, wherein the causing the pair of pivoting catches to pivot comprises engaging the first and second openings of the at least one sensor strip via respective first and second hooks defined respectively along the pair of pivoting catches.

4. The method of claim 1, further comprising removing the meter portion from the container along with the grasped sensor strip, wherein the sensor strip is available to receive a sample after the removing.

5. The method of claim 1, wherein each of the pair of pivoting catches comprises an upper arm, a lower arm, and a pivot point there between.

6. The method of claim 5, wherein the grasping the at least one sensor strip comprises grasping the at least one sensor strip at the first and second openings respectively with the lower arms of the pair of pivoting catches.

7. The method of claim 5, wherein the grasping the at least one sensor strip comprises locking the upper arms of the pair of pivoting catches respectively against a pair of cam elements.

8. The method of claim 7, wherein the pair of cam elements are coupled to one another via a bias element.

9. The method of claim 7, further comprising releasing the at least one sensor strip via a release button that causes the pair of cam elements to move into respective slots of the meter portion, releasing the upper arms of the pair of pivoting catches.

10. The method of claim 1, wherein the grasping the at least one sensor strip comprises pushing the read-head toward the at least one sensor strip via a spring that tensions the sensor strip about the read-head.

11. The method of claim 1, further comprising bending upward a left section and a right section relative to an intermediate section of the at least one sensor strip prior to the inserting the meter portion.

12. The method of claim 1, further comprising providing the at least one sensor strip with a raised section prior to the inserting the meter portion.

* * * * *